(12) United States Patent
Munger et al.

(10) Patent No.: US 7,896,498 B2
(45) Date of Patent: Mar. 1, 2011

(54) APPARATUS AND METHOD FOR OPTICAL MEASUREMENTS

(75) Inventors: Rejean Munger, Orleans (CA); Neil Lagali, Ottawa (CA)

(73) Assignee: Ottawa Hospital Research Institute, Ottawa (CA)

( * ) Notice: Subject to any disclaimer, the term of this patent is extended or adjusted under 35 U.S.C. 154(b) by 0 days.

(21) Appl. No.: 12/414,437

(22) Filed: Mar. 30, 2009

(65) Prior Publication Data
US 2010/0245764 A1 Sep. 30, 2010

(51) Int. Cl.
*A61B 3/10* (2006.01)
*A61B 3/00* (2006.01)

(52) U.S. Cl. .......... 351/221; 351/213; 351/215; 351/246

(58) Field of Classification Search .................. 351/200, 351/205, 206, 213, 214, 215, 221, 246
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,569,354 A | 2/1986 | Shapiro et al. | |
| 5,203,328 A | 4/1993 | Samuels et al. | |
| 5,209,231 A | 5/1993 | Cote et al. | |
| 5,267,152 A | 11/1993 | Yang et al. | |
| 5,341,805 A | 8/1994 | Stavridi et al. | |
| 5,361,758 A | 11/1994 | Hall et al. | |
| 5,433,197 A | 7/1995 | Stark | |
| 5,535,743 A | 7/1996 | Backhaus et al. | |
| 5,568,208 A | 10/1996 | Van de Velde | |
| 5,590,660 A | 1/1997 | MacAulay et al. | |
| 5,617,852 A | 4/1997 | MacGregor | |
| 5,747,806 A | 5/1998 | Khalil et al. | |
| 5,757,002 A | 5/1998 | Yamasaki et al. | |
| 5,820,557 A | 10/1998 | Hattori et al. | |
| 5,857,462 A | 1/1999 | Thomas et al. | |
| 5,873,831 A | 2/1999 | Bernstein et al. | |
| 5,919,132 A | 7/1999 | Faubert et al. | |
| 5,973,779 A | 10/1999 | Ansari et al. | |
| 6,025,597 A | 2/2000 | Sterling et al. | |

(Continued)

FOREIGN PATENT DOCUMENTS

EP 0941692 B1 9/2002

(Continued)

OTHER PUBLICATIONS

Davenport, C.M. Connor; Alexander, A.L.; Gmitro, a.F.; "Optimal fluorescence imaging of atherosclerotic human tissue"; 1991, Proceedings of SPIE — the International Society for Optical Engineering, vol. 1425, Pp. 16-27.

(Continued)

*Primary Examiner* — Jack Dinh
(74) *Attorney, Agent, or Firm* — Dunlap Codding, P.C.

(57) ABSTRACT

Disclosed are an apparatus and method for separately detecting and measuring specularly reflected light and diffusely reflected light following illumination of an eye by light. The apparatus and method of the present invention facilitates substantial separation of the diffusely reflected light from light specularly reflected from the eye after passing through one or more elements of the eye, for example, the cornea, lens, retinal vasculature, the nerve fibre layer and/or the photoreceptors. The collection of these separate streams of independent optical signals to appropriate detection systems provides specificity and accuracy in determination of optical properties of one or more elements of the eye.

21 Claims, 4 Drawing Sheets

U.S. PATENT DOCUMENTS

| | | | |
|---|---|---|---|
| 6,079,830 | A | 6/2000 | Kohayakawa |
| 6,094,592 | A | 7/2000 | Yorkey et al. |
| 6,157,041 | A | 12/2000 | Thomas et al. |
| 6,226,082 | B1 | 5/2001 | Roe |
| 6,278,889 | B1 | 8/2001 | Robinson |
| 6,307,634 | B2 | 10/2001 | Hitzenberger et al. |
| 6,313,914 | B1 | 11/2001 | Roe |
| 6,405,069 | B1 | 6/2002 | Oraevsky et al. |
| 6,409,345 | B1 * | 6/2002 | Molebny et al. .............. 351/212 |
| 6,477,394 | B2 | 11/2002 | Rice et al. |
| 6,503,478 | B2 | 1/2003 | Chaiken et al. |
| 6,504,614 | B1 | 1/2003 | Messerschmidt et al. |
| 6,528,809 | B1 | 3/2003 | Thomas et al. |
| 6,536,900 | B2 | 3/2003 | Mihashi et al. |
| 6,544,212 | B2 | 4/2003 | Galley et al. |
| 6,565,210 | B2 | 5/2003 | Kobayashi et al. |
| 6,574,490 | B2 | 6/2003 | Abbink et al. |
| 6,629,761 | B1 | 10/2003 | Hirohara et al. |
| 6,646,738 | B2 | 11/2003 | Roe |
| 6,650,915 | B2 | 11/2003 | Routt et al. |
| 6,726,326 | B2 | 4/2004 | Fukuma et al. |
| 6,816,241 | B2 | 11/2004 | Grubisic |
| 6,824,269 | B2 | 11/2004 | Takeuchi et al. |
| 6,825,044 | B2 | 11/2004 | Zheng et al. |
| 6,853,457 | B2 | 2/2005 | Bjarklev et al. |
| 6,958,809 | B2 | 10/2005 | Sterling et al. |
| 7,050,157 | B2 | 5/2006 | Braig et al. |
| 2002/0041166 | A1 | 4/2002 | Grubisic |
| 2002/0151774 | A1 | 10/2002 | Soller et al. |
| 2003/0032064 | A1 | 2/2003 | Soller et al. |
| 2003/0086073 | A1 | 5/2003 | Braig et al. |
| 2003/0090649 | A1 | 5/2003 | Sterling et al. |
| 2003/0128333 | A1 | 7/2003 | Fukuma et al. |
| 2003/0143116 | A1 | 7/2003 | Zheng et al. |
| 2003/0184758 | A1 | 10/2003 | Bjarklev et al. |
| 2004/0005717 | A1 | 1/2004 | Soller |

FOREIGN PATENT DOCUMENTS

| | | |
|---|---|---|
| EP | 01437084 A1 | 9/2002 |
| EP | 1232722 B1 | 5/2005 |
| WO | WO 91/017696 | 11/1991 |
| WO | WO 93/07801 | 4/1993 |
| WO | WO 02/071932 A1 | 9/2002 |
| WO | WO 02/088818 A1 | 11/2002 |
| WO | WO 03/076883 A2 | 9/2003 |
| WO | WO 2004/070368 | 8/2004 |

OTHER PUBLICATIONS

Nie, S.; Li, Y.; Redd, D.C.B. ; Yu, N. T. ; "Pattern recognition algorithms for tissue near-infrared FT-Raman spectroscopy"; 1991, Proceedings of the Annual Conference on Engineering in Medicine and Biology, vol. 13, No. 4, pp. 1747-1748..

Domjan, G.; Kaffka, K.J; Jako, 3.M.; Valyi-Nagy, I.T.; "Rapid analysis of whole blood and blood serum using near infrared spectroscopy"; 1994, J. Near Infrared Spectrosc., vol. 2, No. 2, pp. 67-78.

Itzkan, I.; "Real time excitation-emission spectra for in vivo disease diagnosis"; 1996, Conference Proceedings, LEOS '96 9th Annual Meeting. IEEE Lasers and Electro-Optics Society 1996 Annual Meeting (Cat. NO.96CH35895), vol. 1, pp. 3301, Copyright 1997, IEE.

Werner, G.; Fruh, J.; Keller, F.; Greger, H.; Somorjai, R.; Dolenko, B.; Bocker, D.; "Mid infrared spectroscopy as tool for disease pattern recognition from human blood"; 1998, Proceedings of SPIE — the International Society for Optical Engineering, vol. 3257, pp. 35-41.

Ge, Z.; Schomacker, K.T.; Nishioka, N. S.; "Identification of colonic dysplasia and neoplasia by diffuse reflectance spectroscopy and pattern recognition techniques"; 1998, Applied Spectroscopy, vol. 52, No. 6, pp. 833-839.

L.; Sukuta, S.; Bruch, R.F.; Afanasyeva, N. I.; Looney, C.G.; "Tumor diagnosis using backpropagation neural network method"; 1998, Proceedings of SPIE — the International Society for Optical Engineering, vol. 3257, pp. 273-283.

Wu, C.; Kenny, M.A.; Huang, M.C.; Afromowitz, M.A.; Yager, P.; "Feasibility study of the spectroscopic measurement of oxyhemoglobin using whole blood without pretreatment"; 1998, Analyst (Cambridge, U.K.), vol. 123, No. 3, pp. 477-481.

Rodushkin, I.; Ödman, F.; Branth, S.; "Multielement analysis of whole blood by high resolution inductively coupled plasma mass spectrometry"; 1999, Fresenius Journal of Analytical Chemistry, vol. 364, No. 4, pp. 338-346.

Koo, T.W.; Berger, A.J.; Itzkan, I.; Horowitz, G., Feld, M.S.; "Reagentless blood analysis by near-infrared Raman spectroscopy"; 1999, Diabetes Technol Ther, pp. 153-7.

Dam, J.S.; "Optical analysis of biological media: Continuous wave diffuse spectroscopy"; 2000, Lunds Universitet (Sweden) vol. 62-01C, pp. 111.

Petrich, W.; Dolenko, B.; Fruh, J.; Ganz, M.; Greger, H.; Jacob, S.; Keller, Nikulin, a.E.; Otto, M.; Quarder, O.; Somorjai, R.L.; Staib, A.; Werner, Wielinger, H.; "Disease pattern recognition in infrared spectra of human sera with diabetes mellitus as an example"; 2000, Applied Optics, vol. 39, No. 19, pp. 3372-3379.

Petrich, W.; Dolenko, B.; Fruh, J.; Greger, H.; Jacob, S.; Keller, F.; Nikulin, A.; Otto, M.; Quarder, O.; Somorjai, R.; Staib, A.; Werner, G.; Wielinger, H.; "Recognition of disease-specific patterns in FT-IR spectra of human sera"; 2000, Proceedings of the SPIE — the International Society for Optical Engineering, vol. 3918, pp. 91-6.

Vikinge, T.P.; Hansson, K.M.; Sandstrom, P.; Liedberg, B.; Lindahl, T.L.; Lundstrom, I.; Tengvall, P.; Hook, F.; "Comparison of surface plasmon resonance and quartz crystal microbalance in the study of whole blood and plasma coagulation"; 2000, Biosensors & Bioelectronics, vol. 15, No. 11-12, pp. 605-613.

Wei-Chiang Lin; Toms, S.A.; Jansen, E.D.; Mahadevan-Jansen, A.; "Intraoperative application of optical spectroscopy in the presence of blood"; 2001, IEEE Journal of Selected Topics in Quantum Electronics, vol. 7, No. 6, pp. 996-1003.

Tafeit, E.; Horejsi, R.; Sudi, K.; Berg, A.; Reibnegger, G.; Moller, R.; "Optical body fat measurement might contribute to the search for a predictor of type-2 diabetes mellitus"; 2001, Proceedings of the SPIE — the International Society for Optical Engineering, vol. 4432, pp. 293-298.

Sato, H.; Chiba, H.; Tashiro, H.; Ozaki, Y.; "Excitation wavelength-dependent changes in Raman spectra of whole blood and hemoglobin: Comparison of the spectra with 514.5-, 720-, and 1064-nm excitation"; 2001, J Biomed Opt 6(3), pp. 366-70.

Meglinski, I.V.; Korolevich, A.N.; Greenhalgh, D.A.; "Application of low scattering photon correlation spectroscopy for blood monitoring"; 2001, Proceedings of the SPIE — the International Society for Optical Engineering, Vol. 4432, Pp. 24-8, Copyright 2002, Iee, Spie-Int. Soc. Opt. Eng.

Levin, A.D.; Pribytkov, V.A.; Rukin, E.M.; Seregina, I.F.; "Atomic-absorption spectrometry in the elemental analysis of biological materials"; 2001, Measurement Techniques, vol. 44, No. 6, pp. 660-8.

Koo, Tae-Woong; "Measurement of blood analytes in turbid biological tissue using near-infrared Raman spectroscopy"; 2001, Massachusetts Institute of Technology, vol. 63-01B, pp. 377.

Petrich, W.; Dolenko, B.; Fink, D.J.; Fruh, J.; Greger, H.; Jacob, S.; Keller, F.; Nikulin, A.; Otto, M.; Pessin-Minsley, M.S.; Quarder, O.; Somorjai, R.; Staib, A.; Thienel, U.; Werner, G.; Wielinger, H.; "Disease pattern recognition in FT-IR spectra of human sera"; 2001, Proceedings of SPIE — the International Society for Optical Engineering, vol. 4254, pp. 72-80.

Beach, J.; "Spectral reflectance technique for retinal blood oxygen evaluation in humans"; 2002, Proceedings 31st Applied Imagery Pattern Recognition Workshop from Color to Hyperspectral: Advancements in Spectral Imagery Exploitation, AIPR, pp. 117-23.

Enejder A.M.K.; Tae-Woong Koo; Jeankun O.; Hunter, M.; Sasic, S.; Feld, M.S.; Horowitz, G.L.; "Blood analysis by Raman spectroscopy"; 2002, Optics Letters, vol. 27, No. 22, pp. 2004-6.

Fruh, J.; Jacob, S.; Dolenko, B.; Haring, H.; Mischler, R.; Quarder, O.; Renn, W.; Somorjai, R.L.; Staib, A.; Werner, G.; Petrich, W.; "Diagnosing the predisposition for diabetes mellitus by means of mid-Ir spectroscopy"; 2002, Proceedings of the SPIE — the International Society for Optical Engineering, vol. 4614, pp. 63-9.

Hattery, D.; Hassan, M.; Demos, S.; Gandjbakhche, A.; Hyperspectral imaging 2002, Proceedings 31$^{st}$ Applied Imagery Pattern Recognition Workshop from Color to Hyperspectral: Advancements in Spectral Imagery Exploitation, AIPR, pp. 124-30.

Hirsch, L.R.; Halas, N. J.; West, JL.; "A rapid, near infrared, whole blood immunoassay using metal nanoshells"; 2002, Second Joint EMBS-BMES Conference, 24th Annual International Conference of the Engineering in Medicine and Biology Society, vol. 2, pp. 1646-7.

Korolevich, a.N.; Prigun, N. P.; "Statistical characteristics of quasi-elastically scattered light in analysis of size of aggregated biological particles"; 2002, Optics and Spectroscopy, vol. 93, No. 6, pp. 894-8.

Lavine, B.K.; Davidson, C.E.; Moores, A.J.; "Genetic algorithms for spectral pattern recognition"; 2002, Vibrational Spectroscopy, vol. 28, No. 1, pp. 83-95.

Petrich, W.; Staib, A.; Otto, M.; Somorjai, R.L.; "Correlation between the state of health of blood donors and the corresponding mid-infrared spectra of the serum"; 2002, Vibrational Spectroscopy, vol. 28, No. 1, pp. 117-129.

Prohaska, C.; "Adaptation of atomic spectrometric methods for the determination of trace elements in whole blood and blood fractions/ Adaptierung atomspektrometrischer methoden zur bestimmung von spurenelementen in vollblut and blutfraktionen"; 2002, Thesis Reference Number:D 32.229.

Rautray, T.R.; Vijayan, V.; Hota, P.K.; "Elemental analysis of blood in oral cancer"; 2002, International Journal of Pixe, vol. 12, No. 1-2, pp. 41-46.

Savateeva, E.V.; Karabutov, A.A.; Solomatin, S.V.; Oraevsky, A.A.; "Optical properties of blood at various levels of oxygenation studied by time-resolved detection of laser-induced pressure profiles"; 2002, Proceedings of the SPIE — the International Society for Optical Engineering, vol. 4618, pp. 63-75.

Zhang, L.; Small, G.W.; Haka, A.S.; Kidder, L.H.; Lewis, E. Neil; "Classification of Fourier transform infrared microscopic imaging data of human breast cells by cluster analysis and artificial neural networks"; 2003, Applied Spectroscopy, vol. 57, No. 1, pp. 14-22.

Stocker, P.; Lesgards, J.F.; Vidal, N.; Chalier, F.; Prost, M.; "ESR study of a biological assay on whole blood, antioxidant efficiency of various vitamins"; 2003, Biochimica et Biophysica Acta, vol. 1621, No. 1, pp. 1-8.

Schneider, I.; "Raman technique enables noninvasive blood test"; 2003, Laser Focus World, vol. 39, No. 3, pp. 30-32.

Roggo, Y.; Duponchel, L.; Ruckebusch, C.; Huvenne, J.-P.; "Statistical tests for comparison of quantitative and qualitative models developed with near infrared spectral data"; 2003, Journal of Molecular Structure, vol. 654, No. 1-3, pp. 253-62.

Ohtsuki, S.; Hata, T.; Hori, S.; Nagai, Y.; Tomi, M.; Hosoya, K.; Tetsuya, T.; "Differential display analysis of the blood-brain and blood-retina barrier, and function of the brain barrier Selective Gene"; 2003, Society for Neuroscience; Abstract No. 106.4, vol. 2003.

Madhuri, S.; Vengadesan, N.; Aruna, P.; Koteeswaran, D.; Venkatesan, P.; Ganesan, S.; "Native fluorescence spectroscopy of blood plasma in the characterization of oral malignancy"; 2003, Photochem Photobiol, vol. 78, No. 2, pp. 197-204.

Turkes, S.; Korkmaz, M.; Korkmaz, O.; "Time course of the age-related alterations in stored blood"; 2003, Biophysical Chemistry, vol. 105, No. 1, pp. 143-150.

Cote, G.L.; "Noninvasive and minimally-invasive optical monitoring technologies"; 2004, Journal of Nutrition 131/5 (1596S-1604S), Copyright 2004, Elsevier B.V., Amsterdam.

Khoobehi, B.; Et Al.; "Non-invasive measurement of oxygen saturation in optic nerve head tissue"; 2004, Proc. SPIE, Optical Diagnostics and Sensing IV, vol. 5325, pp. 104-110.

Moecks, J.; Kocherscheidt, G.; Koehler, W.; Petrich, W.H.; Progress in diagnostic pattern recognition (DPR); 2004, Proceedings of the SPIE — the International Society for Optical Engineering, vol. 5321, No. 1, pp. 117-23.

* cited by examiner

APPARATUS AND METHOD FOR OPTICAL MEASUREMENTS

CROSS REFERENCE TO RELATED APPLICATIONS

This application claims priority to and benefit under 35 U.S.C. §§119 and 365 of International Application PCT/CA2007/001753, filed Oct. 1, 2007; which in turn, claims priority to U.S. Provisional Application No. 60/827,585, filed Sep. 29, 2006; the entire contents of International Application No. PCT/CA2007/001753 and U.S. Provisional Application No. 60/827,585 are hereby expressly incorporated herein by reference.

FIELD OF THE INVENTION

The field of the invention generally relates to an apparatus and method for optical measurements. More specifically, the field of the invention relates to an apparatus and method for separately detecting and measuring specular reflection and diffusely reflected light emitted following illumination of an eye.

BACKGROUND

Determination of the concentration of solutes in bodily fluids is often used for monitoring of medical conditions and treatments, diagnostics, health assessment, early disease indication and the like. Typically, the determination of the concentration of solutes in a bodily fluid requires invasive procedures, such as the drawing of blood, for diagnostic measurements. However, the drawing of blood can be a painful experience for a patient and it provides a degree of risk to the health care provider, vis-à-vis infectious disease, when drawing and handling a patient's blood. Furthermore, subsequent diagnostic measurements can be time consuming and expensive to perform. Desirably, a non-invasive diagnostic apparatus and method would permit collection and analysis of information regarding the concentration of bodily fluid solutes.

Non-invasive procedures have been developed that use the eye, and in particular the retina, of a subject to monitor and measure specific analyte concentrations. Examples of such non-invasive procedures include: glucose sensing through aqueous humor; reflectance of retina to determine haemoglobin, glucose, oxygen; and raman to measure macular carotenoid levels. However, these presently known approaches have had a number of drawbacks. Typically, current techniques suffer from poor sensitivity to changes in biochemical indicators within the fluid (e.g., blood) or tissue. The result is reduced accuracy in indicator quantification and therefore reduced reliability in determining the state of the blood and the health of the subject. To date, these shortcomings have precluded the acquisition of meaningful and reliable optical signals from the retinal tissue and have prevented widespread adoption of such methods.

U.S. Pat. No. 6,565,210 describes an ocular characteristic measuring apparatus capable of measuring a light-intensity distribution characteristic of a target image formed on a fundus of an eye and of determining the ocular optical characteristic of the eye on the basis of the measured light-intensity distribution characteristic. The disclosed device apparently removes "substantially all" scatter-reflected light from the light reflected from the fundus.

U.S. Pat. No. 5,919,132 discloses a method and apparatus for conducting on-line and real-time spectroreflectometry oxygenation measurement in a patient's eye following illumination of the eye. The device comprises a first optical system to transmit the axial central portion of a light beam reflected from the fundus of the patient's eye to a detector for spectroreflectometry oxygenation measurements. Further, the device comprises a second optical system for transmitting the axial peripheral portion of the reflected light beam to a second detector for visualizing the fundus of the patient's eye and positioning the light beam on the fundus without positioning error.

There remains a need for a reliable and accurate non-invasive method and apparatus for obtaining optical measurements useful in monitoring the health of a subject and/or of a retina of a subject.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an apparatus and method for optical measurements. In accordance with one aspect of the present invention, there is provided an optical apparatus, comprising: (a) an illumination system comprising a light source for illuminating one or more elements of an eye of a subject; (b) an optical separation means for separating light specularly reflected from one or more component of said eye from diffusely reflected light returned from said eye; (c) a detection system comprising: one or more detectors; and transmission means for collecting and separately transmitting the separated specularly reflected light and the diffusely reflected light to said one or more detector, and (d) an eye/instrument interface for controlling light delivery from said illumination system to said eye and for capturing and transmitting light exiting the eye to said detection system. The term "diffusely reflected light" is used herein to refer to all light returned from the eye excluding the specularly reflected light. Diffusely reflected light includes, but is not limited to, fluorescence, auto-fluorescence, scattered light, such as back-scattered light, multiply-scattered light and raman-scattered light.

In accordance with another aspect of the present invention, there is provided a method for monitoring light remitted from an eye of a subject comprising the steps of: illuminating one or more element of said eye with a light source; transmitting light specularly reflected from said eye to a detection system via an optical separation means; and separately transmitting diffusely reflected light remitted from said eye to said detection system.

DETAILED DESCRIPTION OF THE INVENTION

Figure 1:
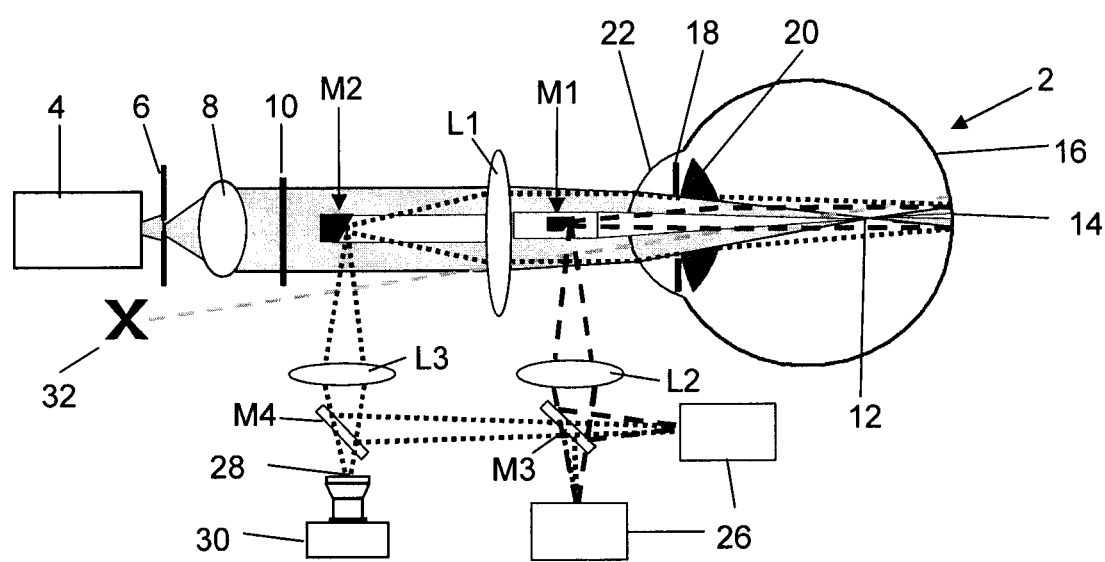
FIG. 1 is a schematic representation of an apparatus according to an embodiment of the present invention (illumination depicted by shaded areas, retinal absorption is depicted by dashed lines and scatter is depicted by dotted lines).

As will be described in more detail below, the present invention provides an apparatus and a method for separately detecting and measuring specularly reflected light and diffusely reflected light following illumination of an eye by light. The apparatus and method of the present invention facilitates substantial separation of the diffusely reflected light from light specularly reflected from the eye after passing through one or more elements of the eye, for example, the cornea, lens, retinal vasculature, the nerve fibre layer and/or the photoreceptors. The collection of these separate streams of independent optical signals to appropriate detection systems provides specificity and accuracy in determination of optical properties of one or more elements of the eye.

The apparatus of the present invention facilitates illumination of one or more elements of an eye of a subject. The illumination light is focussed through the eye to a spot at or near the focal point of the spherical retinal reflecting surface. As the light diverges from its focal point, it interacts with the retinal tissue and the specular reflection from the deepest layers of the retina exits as a beam having a vergence modified as a result of its interaction with the specularly reflecting surface. This light contains information relating to the absorption of blood within the retinal and choroidal vessels after passing through the tissue twice (thus increasing absorption). The specularly reflected beam exiting the retina is focussed by the lens of the eye and cornea to an image point in front of the eye (anterior focal point of the eye).

Light that is not specularly reflected is scattered in random directions by the blood, blood vessel surfaces, and/or other tissue or fluid of the back of the eye. Some of this diffusely reflected light is directed back towards pupil and will exit through the lens and cornea of the eye. Since light scattered at the retina is at the focal plane of the eye, the scattered light exits the eye as a beam having a vergence dependent on the refractive error of the eye, for example, scattered light exiting a perfectly corrected eye will exit as a parallel beam.

In accordance with a specific embodiment of the present invention, the apparatus is configured to perform the following three basic data acquisition tasks:

1. Diffuse Imaging: The apparatus collects and detects scattered light including, for example, back-scattered light, multiply-scattered light and raman-scattered light, following illumination of one or more elements of the eye.
2. Auto-fluorescence: Similar to diffuse imaging, the apparatus of the present invention can collect and detect auto-fluorescence. In order to measure auto-fluorescence, the light source delivers light in a lower wavelength range (<500 nm) than for diffuse imaging (>500 nm) so that only the fluorescence signals are recorded. During measurement of auto-fluorescence, it is beneficial to ensure very high rejection of the source wavelength in the detection arm. Detection can be done using different detection wavebands.
3. Specular Reflection: Following illumination, a specular reflection is produced within the inner layers of the tissue in the back of the eye. The apparatus of the present invention takes advantage of the difference in vergence between the diffuse imaging and specular reflection signals to isolate their individual contributions and obtain a spatially resolved measurement of the specular reflection. The same light source(s)/detection combinations used for specular reflection are used for diffuse imaging.

Components of the Apparatus

The apparatus of the present invention comprises a light source, an eye/instrument interface for controlling light delivery to the eye and for capturing and transmitting light exiting the eye; and a detection system that comprises an optical means for separating light specularly reflected from one or more component of said eye from diffusely reflected light returned from said eye. Each component is described in more detail below.

Eye-Instrument Interface

Light emitted from a light source is ultimately used to illuminate one or more elements of an eye of a subject and the light emitted from the eye, as a result of this illumination, is collected and detected. The apparatus of the present invention includes an eye-instrument interface that functions to (i) deliver illumination from the light source to one or more elements of the eye; (ii) collect optical signals from the one or more elements of the eye; and (iii) ensure that the entrance pupil of the eye is conjugate to the exit pupil of the light source, in order to optimize light collection and control retinal illumination.

In accordance with one embodiment of the present invention, the illumination and detection systems within the eye/instrument interface share one or more optical components. This allows for optimization of the detection of the small signal returning from the retina and avoids the need for multiple beamsplitters in the return path. This approach requires very good reflection control in the eye instrument interface, in particular in the light collection side.

Real human eyes can have a refractive error typically ranging from about −12 D to about +8 D. Therefore, in accordance with a particularly advantageous embodiment of the present invention the apparatus includes an eye/instrument interface configured to provide the eye with correction of refractive error with minimal impact on optical quality and pupil matching.

Illumination System

The illumination system of the apparatus of the present invention comprises a light source and optical paths for transmitting light from the light source to one or more elements of an eye of a subject.

Light Source

The apparatus of the present invention includes a light source for illuminating one or more elements of an eye of a subject. The light source, can be, but is not limited to, a lamp (e.g., a tungsten-halogen lamp, an arc lamp or an incandescent lamp), a light emitting diode or a laser (any laser would be suitable for use in the apparatus of the present invention, provided that it is not harmful to the eye). Depending on the application it may be desirable to include within the apparatus of the present invention means for modifying the light emitted by the light source, either in spectral content, beam shape or vergence, or intensity.

In certain applications, the apparatus includes one or more optical filters to improve sensitivity by blocking unwanted wavelength ranges such as those stimulating fluorescence in situations in which fluorescence is not measured, those potentially harmful to the retina, or those absorbed significantly by the blood. An optical filter or filters can also be used to split the explored wavelength range into spectral bands for which separate measurements can be obtained. The use of optical filters can reduce the total retinal light exposure, and allow the light detection to be optimized separately for each spectral band, thereby providing optional sensitivity enhancement.

Further, certain applications benefit from modification of the light source. For example, the apparatus of the present invention optionally includes a pin hole for generating a point light source.

Illumination Paths

In accordance with one embodiment of the present invention, a single optical path for illumination is employed, which is used in the measurement of both specular reflection and diffuse reflection.

In accordance with an alternative embodiment of the present invention, two optical paths for illumination are employed, one for the diffuse imaging images ($I_{sfi}$) and one for the specular reflection measurement ($I_{rfi}$), thereby providing means for separately detecting diffusely reflected light and specularly reflected light.

In the $I_{sfi}$ path, a point source is imaged in the entrance pupil of the eye, ensuring maximal transmission into the eye and producing uniform retinal illumination (Maxwellian view). The goal is uniform or substantially uniform retinal illumination; with known illumination intensity, so that light returning from the retina can be quantified. The Maxwellian view discussed here is the classical implementation used in most ophthalmic instruments requiring uniform retinal illumination.

The cornea will have a strong specular reflection (typically, 2 to 4% of incident light), a significant part of which can return into the imaging optics if the illumination/imaging pathway designs are not configured for its removal.

In the $I_{rfi}$ illumination pathway, the source must be focused inside the eye, so that the specular reflection from the reflecting surface in the deep retina has a vergence that is easily separated from the scatter image. For example, the specular reflection light source can be adapted to focus at a point in the eye so that the reflected image is focused in the eye's pupil, thereby maximize the capture of the reflected light exiting the eye. Other solutions are possible, provided the required specularly reflected image is obtained. An advantage of the image being formed at the pupil plane is the ability to use the same optical system for the pupil size measurement.

The illumination system optionally includes means for controlling the vergence of the light in the eye. In this way, by using the apparatus of the present invention it is possible to control the depth of the focal point of the light in the eye of the subject. Vergence control means optionally include means for collimating the beam of light emitted from the light source, for example, a microscope objective, a lens or a combination of lenses. Alternatively or in addition, the light source or one of the lens is movable on a single axis translation stage, which permits movement of the point of focus in the eye.

Detection System

The apparatus of the present invention includes a detection system for separately detecting specular reflection and diffusely reflected light following illumination of an eye of a subject. The specular reflection is substantially free of diffusely reflected light. The detection system comprises one or more detectors and optical means for separating and transmitting the light collected by the eye/instrument interface to the one or more detectors. The means for separating and transmitting the light can be a lens, a mirror, a prism, a beam-splitter, a blocking aperture or any combination thereof.

The apparatus of the present invention is configured such that light exiting the eye for detection does not pass through the same corneal area as the light entering the eye from the illumination system.

Diffuse (Scatter/Auto-Fluorescence) Detection Path

The purpose of the diffuse detection path is to focus the light originating from the retina through scatter, including in some instances auto-fluorescence, onto a detection system including a detector, such as, but not limited to a high spatial resolution detector. Scatter signal can be obtained in a range of bandwidths ranging from 400 to 1300 nm, for example, from 450 to 1000 nm. In accordance with an advantageous embodiment of the present invention, the optical system of the diffuse path is close to the diffraction limited resolution. At a minimum the optical system exceeds ocular resolution over the whole range of wavelengths measured for pupil diameters larger than or equal to 4 mm.

The diffuse detection path optionally includes spectral selection filters to obtain images at different wavelength bandwidths for auto-fluorescence as well as neutral density filters for optical power control.

The diffuse detection path also optionally includes means for imaging a 45 degree field of the retina on, for example, a high spatial resolution detector (CCD) in the detection system.

Specular Reflection Detection Path

The optical elements in the specular reflection detection path must be able to focus the specular reflection signal onto a detector after its interaction with the retina. The specular reflection detection path is configured to (i) minimize the impact from the diffusely reflected signal; (ii) optimize the specular reflection signal exiting the eye to ensure accurate quantification of return signal; and (iii) provide the same wavelength properties as described above for the diffuse detection pathway.

Detectors

The detection system comprises one or more detector for detecting and/or measuring the light emitted from the eye as specular reflection, scatter and/or autofluorescence. Each detector can be, for example, a spectrophotometer, a camera, a photodiode or a bolometer.

Use of the Apparatus

Use of the apparatus of the present invention will be described in more detail herein with reference to the specific embodiments depicted in FIGS. 1, 2A, 2B and 3 and described below. It should, however, be understood that the present invention is not limited to the specific embodiments depicted in FIGS. 1, 2A, 2B and 3.

A specific embodiment of the apparatus of the present invention is depicted in FIG. 1. With specific reference to FIG. 1, an eye 2 is illuminated with tungsten-halogen lamp 4 providing light having a broad wavelength range (400-1400 nm). Pinhole 6 is used to create a point source while microscope objective 8 is used to collimate the beam of light (illumination beam). Optical filters 10 can be used to block unwanted wavelength ranges, such as those stimulating fluorescence, those potentially harmful to the retina, or those absorbed significantly by the blood. Optical filters 10 can also be used to split the explored wavelength range into spectral bands for which separate measurements can be taken. Lens L1 is positioned such that the collimated illumination beam is focused through eye 2 to spot 12 at the focal point of spherical retinal reflecting surface 14 (about 5.5 mm in front of the retina). As the light diverges from spot 12, the light interacts with the retinal tissue (not shown), some light is absorbed by the tissue, some light is specularly reflected and some light is diffusely reflected. The specular reflection from the deepest layers of the retina (not shown) exits as a parallel beam (dashed lines in FIG. 1). Illumination spot 13 on retina 16 has a diameter of about ⅓ the diameter of the pupil diameter. If needed the pupil size can be varied by darkening the room or by using eye drops or other methods, as would be readily apparent to the skilled worker.

The specularly reflected light exiting retina 16 is focused by lens 20 and cornea 22 of eye 2 to a point image in front of the eye (anterior focal point of the eye), where a small mirror M1 directs the light to a detection system. Lens L2 focuses the light onto the entrance slit of either of two separate spectrometers 26, through use of a double-sided movable mirror M3. By way of example, spectrometers from Ocean Optics may be used, as they permit rapid, sensitive, high-resolution detection of a broad range of wavelengths (400-1400 nm) in a compact footprint at a reasonable cost. Other types of suitable spectrometers will be well known to the skilled worker.

As described above, light that is not absorbed or specularly reflected is scattered by the blood and blood vessel surfaces in random directions and a portion is directed back towards pupil 18, and will exit through lens 20 and cornea 22 of eye 2 as a parallel beam (dotted lines in FIG. 1), assuming that eye 2 is perfectly corrected. Lens L1 focuses this parallel beam to a point on small mirror M2, which directs the light to lens L3 and also serves to spatially filter out scattered light not originating at the retinal plane. Lens pairs L1-L3 and L1-l2 are arranged such that they create a conjugate image of the pupil plane at camera pupil 28, while the camera detector 30 is conjugate to the retina. In this manner, the maximal amount of light is delivered to camera 30. The image obtained from the camera is an aid for the operator in alignment of the illumination spot (for both absorption and scatter) on the patient's retina.

The patient's visual axis may be controlled through the use of fixation target 32 to move the illuminated area of the retina to a point at least 5 degrees off-axis to avoid the avascular macular region. Reproducibility of the measurement area between sessions is ensured through acquisition of an image of the measurement spot on the patient's retina. Similar approaches have been used to align the patient's retinal measurement area for oximetry and optical coherence tomography (OCT) imaging. Once a measurement area has been chosen, a movable mirror M4 is used to direct the diffusely reflected light to a focal point on the entrance slit of either of the spectrometers 26, depending on the presence or absence of the movable mirror M3.

Use of the apparatus of the present invention in accordance with the embodiment depicted in FIG. 1, permits simultaneous measurement of diffuse light and specularly reflected light exiting the eye following illumination.

Figure 2A:
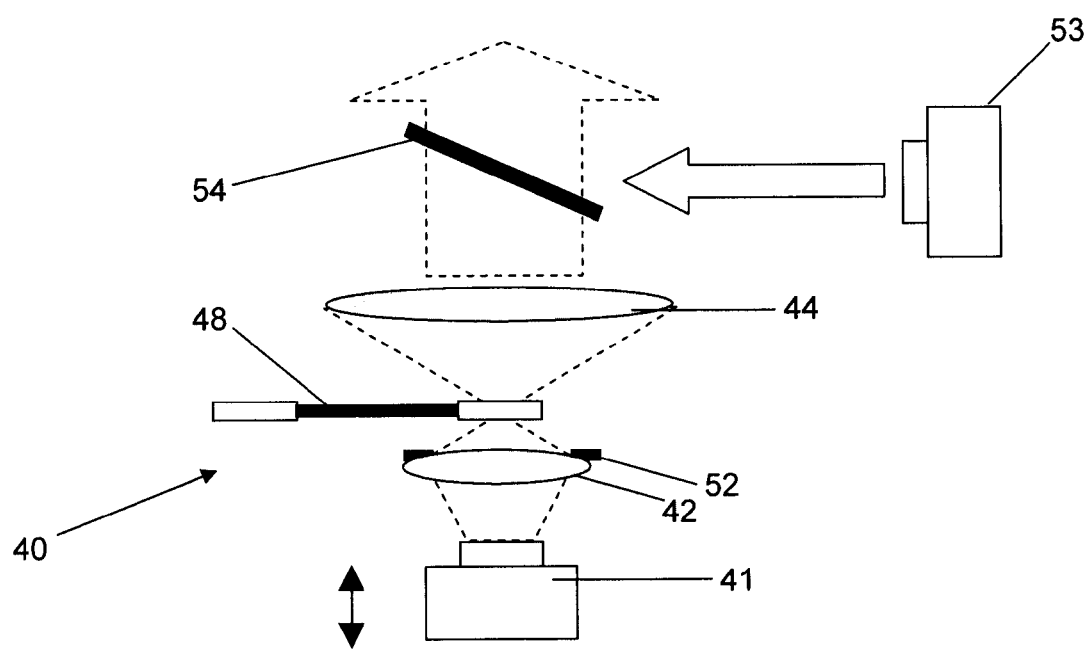
FIG. 2A is a schematic representation of an illumination system suitable for use in an apparatus according to an embodiment of the present invention (illumination depicted by dashed lines)
Figure 2B:
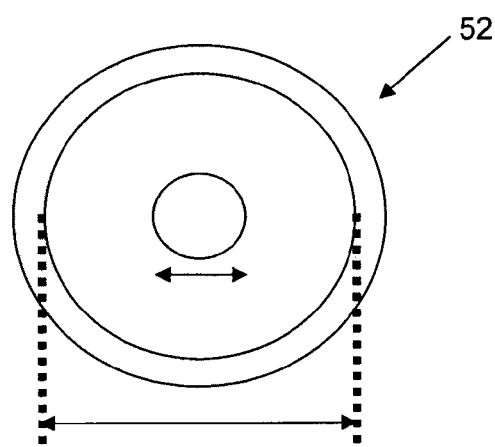
FIG. 2B provides a detail schematic of an illumination aperture for use in the illumination system depicted in FIG. 2A.
Figure 3:
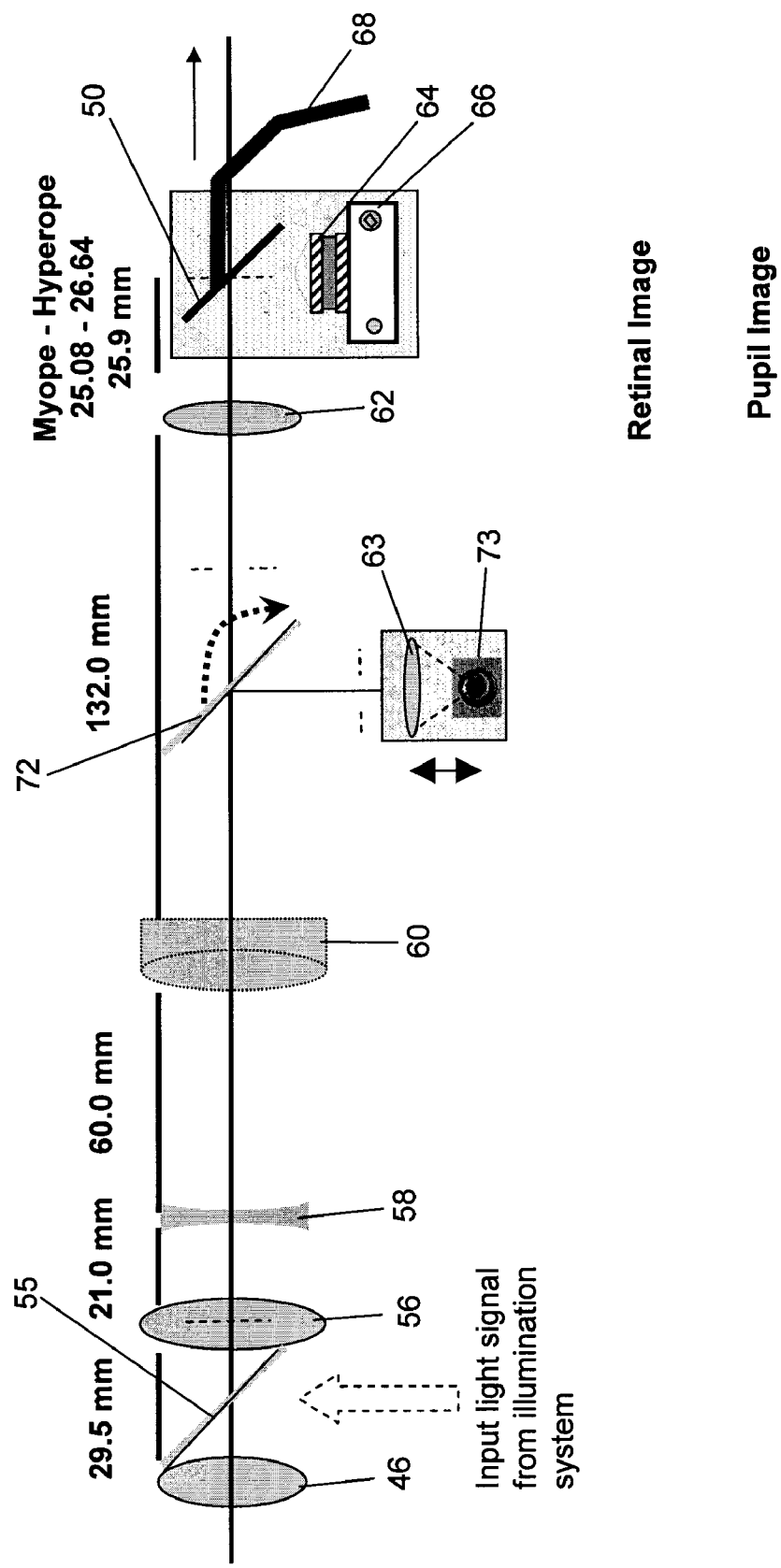
FIG. 3 is a schematic representation of an apparatus according to an embodiment of the present invention.

An alternative embodiment of the apparatus of the present invention is depicted in FIGS. 2A, 2B and 3.

The illumination system comprises optical source 40 (FIG. 2A). Optical source 40 is used to illuminate the eye of a subject with light. Optical source 40 includes a narrow band or broadband light source as required by the particular application of the apparatus. The two lenses (42 and 44) are used to control the properties of the light entering the eye (vergence and magnification of source) so that it can be focused at a selected point in the eye and provide required illumination when combined with the lens 46 positioned directly in front of the eye (FIG. 3). For example, to illuminate the eye for a classical fundus photograph the light can be focused in the entrance pupil of the eye.

In the implementation depicted in FIG. 2A, light source 41 is a broadband light source (for example: Mercury or Xenon arc lamp, halogen lamp). The spectral properties of light source 41 are selected via filter wheel 48 containing many filters (not shown), each with its unique spectral transmission. In one embodiment of the present invention, filter wheel 48 comprises neutral density (ND) filters for controlling intensity, which can be used individually or in combination with spectral filters. The location of the spectral/ND filters is not critical, provided that it is in the illumination path but not in the light capture path (i.e., lens 46 to mirror 50 as shown in FIG. 3) and that the spectral properties of the filters take into account the vergence of the light incident on the filter. In the embodiment depicted in FIG. 2A, the plane selected is at the image plane of light source 41 so that the area of the interaction of the light with the filter is as small as possible. This can reduce cost and improve uniformity of transmitted light because of reduced chances of filter variation in a smaller filter area than in a larger filter area.

Lenses 42 and 44 serve several purposes. Optically, they control vergence and beam diameter for the illumination of the eye. Vergence can be modified by moving either lens, depending on other requirements of the system. The use of two lenses provides better control over the optical properties while providing the opportunity to introduce beam modification apparatus as necessary. However, a worker skilled in the art would readily appreciate that it is not necessary to include two lenses in an optical source for successful use in the apparatus of the present invention.

In the embodiment depicted in FIG. 2A, means for two beam modifications are provided, namely the filters in filter wheel 48, which control spectral/intensity, and aperture 52 at the face of one of the lenses, which blocks the center of the beam. A detail of aperture 52 is provided in FIG. 2B. Lenses 42 and 44 are selected such that aperture 52 is conjugate with the corneal apex, so that no light is incident on the centre of the cornea. This means that there is no specular reflection from the corneal apex that returns to the detection arms to act as a diffuse source of light in retinal images. As noted above, when describing the detection system, the corneal area is split into illumination and collection areas such that light exiting the eye for detection does not pass through the same corneal area as light entering the eye from the illumination system.

As depicted in FIG. 2A flip mirror 54 can be incorporated in the optical source pathway to allow supplementation of broadband light source 41 by a second light source 53. For example, to obtain auto-fluorescence from the retina of an eye of a subject, a white light source might not have sufficient intensity in the blue to UV part of the spectrum. By adding a light emitting diode as second light source 53 and using flip mirror 54 the diode can replace broadband light source 41 when blue illumination is required. In general, the optical source of the apparatus of the present invention can include multiple light sources to perform all required tasks. The use of multiple light sources can be facilitated, for example, by using multiple mirrors (including, but not limited to, dichroic, flipped in and out or permanent) to merge or select the different light sources.

As depicted in FIG. 3, illumination light exits optical source 40 and moves to the eye/instrument interface where it is directed by beamsplitter 55 to lens 46, which, in turn, focuses the illumination light at one or more elements of an eye of a subject. Light is subsequently emitted from the eye in the form of diffusely reflected light, which may include autofluorescence, and specularly reflected light. Lens 46 is positioned in front of the eye to capture all, or substantially all, of the light emitted from the eye and to introduce some focusing power that relays the light to the rest of the optical system with minimal loss and good image quality. The lens aperture must be large enough to accommodate the highly divergent light exiting the eye of a subject with a large defocus error.

In accordance with a specific embodiment of the present invention, lens 46 will have a diameter of 40 mm or more, its focal length will be less that 40 mm and it will be positioned so its focal plane is close to the entrance pupil of the eye.

Light exiting the eye moves through lenses 46, 56, 58 and 60, which are used to collect the light exiting the eye and relay it to detection systems whether they are imaging, spectral or intensity based. The goal of the instrument is to independently detect light originated at the retina as diffusely reflected, including fluorescence, and light specularly reflected from the reflective layers of the retina. In the embodiment of the invention depicted in FIG. 3, separate detection pathways are provided for each mode but it is possible to use a single detection pathway.

In the apparatus depicted in FIG. 3, lenses 46, 56, 58 and 60 are common to both detection pathways, while lens 62 is unique to the diffuse (scatter and fluorescence) detection pathway and lens 63 is unique to the specular reflection detection pathway. In the diffuse detection pathway lenses 46, 56, 58, 60 and 62 are used to control image magnification and produce a high quality image of the retina at a plane perpendicular to the optical axis behind lens 62. Because of the choice of introducing the illumination through beamsplitter 55 and lens 46 to the eye, there needs to be enough space between lens 46 and the next lens to incorporate beamsplitter 55. This constraint, combined with the need to ensure (i) magnification is compatible with CCD cameras, (ii) full transmission of light from lens 46 to the camera, and (iii) good optical quality (curvature of field, monochromatic aberrations, chromatic aberrations), as well as maintaining component diameters sufficiently small to minimize cost and availability, results in the use of a multiple lens optical design for the diffuse detection pathway. Lens 56 is a collector lens that ensures light collection from lens 46 for the large separation between lenses 46 and 58. Lens 58 is a negative lens to keep the overall design shorter and reduce curvature of field effects in the image. Lenses 60 and 62 are used to match the magnification of lenses 46, 56 and 58 to that required by the CCD camera. The diffuse detection pathway is configured to produce good light capture/transmission and good optical quality for a scatter image.

Because each eye has slightly different refractive power, CCD camera 64 is on stage 66 which moves along the optical axis of the instrument, it is focused on the center of mirror 50 whose center is conjugate with the image. If the eye results in an image further from lens 62 than normal, the mirror/camera assembly is moved away from lens 62 until the image is in focused on CCD camera 64. The opposite movement is made for an image closer to lens 62 than normal. Movement of stage 66 can be manual or motorized. If it is motorized, then movement is controlled by a computer system.

Figure 4:
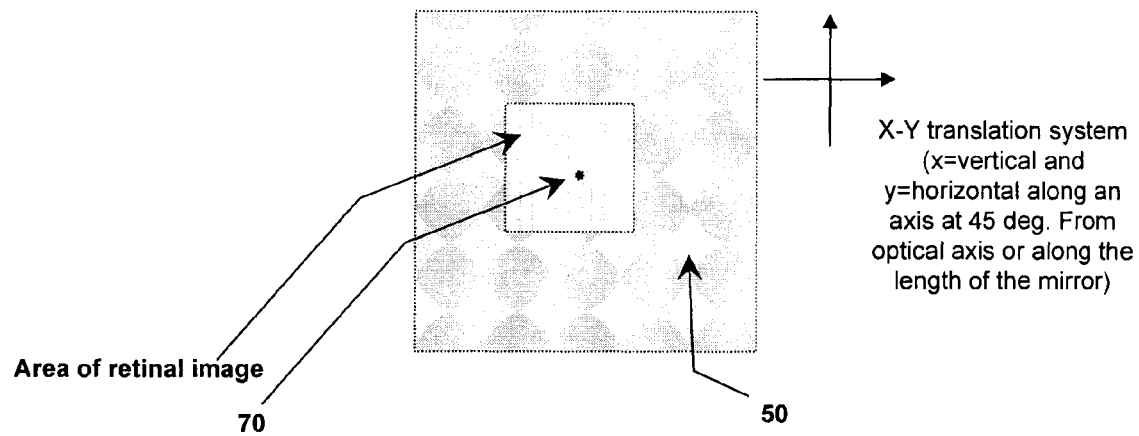
FIG. 4 depicts an image of a retina on a mirror in the light collection path of the apparatus depicted in FIG. 3. The spot in the image of the retina corresponds with the fibre tip of an optical fibre used in the detection system of the apparatus depicted in FIG. 3.

Additionally if spectroscopy of any point on the retina is required, there is a small hole in mirror 50 in which small optical fibre 68, having fibre tip 70, is introduced. Optical fibre 68 is connected at its other end to a fibre coupled spectrometer (not shown). Mirror 50 is large enough that it is possible to image the retina on mirror 50 without overlap with fibre tip 70. When fibre tip 70 is brought into the CCD field of view it appears as a spot in the image of the retina because the light incident of fibre tip 70 is sent to the spectrometer and recorded (see FIG. 4). A combination of using fixation points to rotate the eye and moving mirror 50 (computer or manually controlled) allows the operator to select the point of interest for sampling a spectrum. Fibre tip 70 can be any diameter of choice for an investigation, from small single mode fibre to large multimode fibre as appropriate for the particular investigation.

Figure 5:
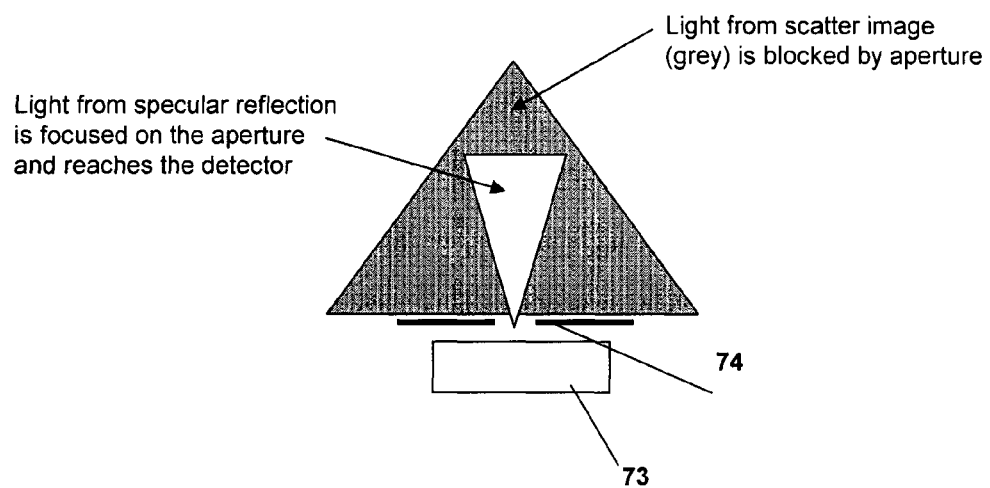
FIG. 5 is a detailed view of a portion of the specular reflection detection path of the detection system of the apparatus depicted in FIG. 3.
Figure 2B:
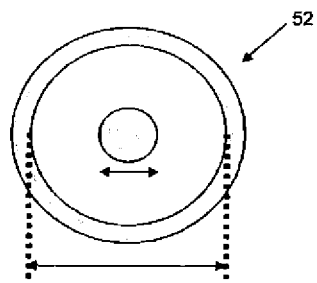
Figure 3:
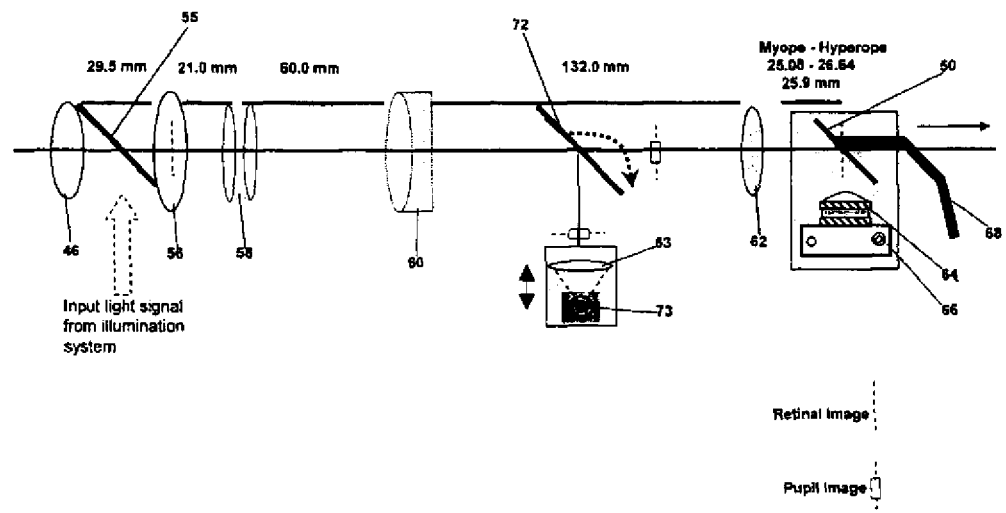

In the use of the apparatus depicted in FIG. 3, measurement of the reflected and diffusely reflected signal are taken consecutively. When flip mirror 72 is introduced between lens 60 and lens 62, all the light is redirected to a single element detector 73 via lens 63. Detector 73 can be, for example, but not limited to, a pin diode, an avalance photodiode or a photomultiplier tube. This light includes both the diffusely reflected and the specularly reflected light. The position of detector 73 is selected so it is conjugate with the light specularly reflected from the retina and thus must move to match that plane based on the refractive power of the eye and the selected point of focus for the light source, which could be different than that used for the scatter imaging. In front of detector 73, a small aperture 74 (see FIG. 5) that matches the size of the specularly reflected light (a point image) is introduced. In this way the light from the specular reflection is passed on to detector 73 while the diffusely reflected light, which forms an image in a different plane, is almost entirely excluded.

The configuration of the apparatus as depicted in FIGS. 2A, 2B and 3 does not permit simultaneous detection, but rather is used to obtain sequential data sets for its flexibility in a research environment.

Alternatively, and not shown in the Figures, an optical fiber also connected to the spectrometer can be placed in the plane of the detector for reflectance in order to obtain spectral information.

The apparatus of the present invention, in accordance with the embodiment depicted in FIGS. 2A, 2B and 3, optionally includes filters in the detection pathways that can be used to minimize interference from environmental light as desired or when auto-fluorescence or fluorescence images are being measured, which requires that all light from the illumination system is blocked from the detection system.

In a further embodiment of the present invention, the apparatus is used to take two measurements; first, to detect all light exiting an eye following illumination and, second, to detect only the diffuse reflection exiting the eye following an identical, or near identical, illumination. Specular reflection exiting the eye is subsequently calculated by subtracting the diffuse reflection (second) measurement from the total (first) measurement using appropriate weighting to account for illumination/detection optical path differences, which includes both diffuse reflection and specular reflection. It should be well understood that the sequence of measurements is not critical to this embodiment and that the terms "first" and "second" measurement are merely used to readily distinguish the measurements.

The measurement of diffuse reflection only can be achieved, for example, by using a polarized light beam for illumination. In this case, light from the light source is polarized as it is transmitted thought the illumination path. Means for transforming unpolarized light into polarized light are well known and can include, for example, a polarizing filter, a polarization beam splitter (linear polarization) and/or a quarter or half wave plate (circularly polarized light). As linearly polarized light interacts with the components of the eye, the specularly reflected light exits with a shift in the linear axis of polarization as compared to the input light. Thus, the specularly reflected light has well understood polarization and can be readily removed from the light emitted from the eye using standard, well known techniques such that the light that reaches the detection system consists of diffuse reflected light only. Similarly, when the input beam is circularly polarized light, the specularly reflected light has a well understood polarization (i.e., left handed becomes right handed and vice versa) and can be readily subtracted from the non-specularly reflected light emitted from the eye using standard, well known techniques. In performing the calculations to quantify the specular reflection and diffuse reflection components of the total light emitted following illumination, it is necessary to take into consideration the change in light intensity resulting from the use of polarization filters, etc. In particular, measurements are appropriately weighted based on the known change in light intensity caused by the specific means for polarization included in the apparatus.

Application of the Apparatus

The present invention also provides a method for obtaining optical measurements following illumination of an eye of a subject. Generally, the method includes the steps of illuminating the eye of a subject with an input light and monitoring specularly reflected light and diffusely reflected light emitted from the eye. The specular reflection is substantially separated from the diffusely reflected light. As set out above, specularly reflected light exits the retinal tissue as a parallel beam and contains information relating to the absorption of blood within the retinal and choroidal vessels and the absorption of retinal tissue itself. The method of the present invention includes the step of substantially separating light exiting the eye as diffusely reflected light from light exiting the eye as a specular reflection. The separated light is then transmitted to an optical sensor or multiple optical sensors for detection.

The method and apparatus of the present invention are useful as part of diagnostic methods for determining and/or monitoring the health of a subject. For example, the method and apparatus of the present invention can be used to detect and measure a specific analyte or analytes within the retinal blood and/or tissue as an indicator of the state of health of the subject. In an alternative embodiment, the method and apparatus of the present invention is not limited to the measurement of a specific analyte or analytes, but rather the composite optical measurement is used as an indicator of the state of health of the subject.

Two exemplary applications of the apparatus and method of the present invention are provided below. As would be readily appreciated by a worker skilled in the art, the present invention is not limited to the two specific examples provided below:

Retinal Health

Retinal tissues, such as the nerve fibre layer, photoreceptors, ganglions cells and many other, interact with light with two important mechanism. The tissues can scatter light or absorb/transmit light both selectively based on the wavelength of the light. The two signals, although not completely independent, do contain different information about the tissue. For example, scatter can be affected by size, index of refraction and absorption more likely by chemical structure. By using both signals, the amount of information that can be obtained regarding the tissue is increased in comparison to that obtainable from measuring only one signal and the ability to detect an abnormality is improved thereby.

The specular reflection which traverses the retina to a reflecting plane in the retina, contains information regarding the effect of tissue absorption due to the retinal tissue above the reflective plane as well as some information (not in focus, but present) about the scatter. The diffusely reflected light measurement focuses only the light diffusely reflected from the retina when applying a removal of the specular reflection. The profile of the scatter contribution is thus obtained and can be removed from that of the specular reflection. Isolation of the two signals is useful to obtain a profile of the optical properties of the retina and, thus, improve on current optical techniques used to detect abnormal tissues.

Choroidal Blood Assessment

The choroid is a vascular type structure located behind the retina and just before the scleral tissue that is the eye's outer shell and gives it its shape. The choroid is responsible for providing the posterior retina (photoreceptors, retinal pigmented epithelium and other neural tissue) with oxygen and nutrients as well as dispose of metabolic waste resulting from the very active metabolism of these tissues. In the central retina (fovea), the choroid is the only such source as no superficial vasculature is present in order to minimize the impact on vision. Thus, for most of the retina, and especially for the fovea, the ability to accurately measure the optical properties of blood are essential to extract medical information from the optical measures.

In a methodology when light is incident on the retina, interacts with it and then returns out of the eye to be detected, this light has interacted not only with the choroid but all other tissues above it. That means that light returning from the retina contains optical information about the combined impact of all the tissue as well as the choroidal blood. By using the instrument of the present invention, it is possible to obtain an accurate measure of the optical properties (mainly absorption) of the tissue above the plane of the specular reflection (deep in the retina) using the specular reflection. Light that travels through the retina to the plane of reflection is specularly reflected through the retina again and then exits the eye. This signal also contains the optical properties of the crystalline lens and the cornea. The diffusely reflected light from the choroid in the fovea will have to travel through the retina, lens and cornea twice as well, but will additionally have interacted with the choroid. It is then simple to the extract the impact of the choroidal blood by taking the ratio of the two signals with proper normalizations.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. An optical apparatus, comprising:
   (a) an illumination system comprising a light source for illuminating one or more elements of an eye of a subject;
   (b) an optical separation means for separating light specularly reflected from one or more component of said eye from diffusely reflected light returned from said eye;
   (c) a detection system comprising:
      (i) one or more detectors; and
      (ii) transmission means for collecting and separately transmitting the separated specularly reflected light and the diffusely reflected light to said one or more detector, and
   (d) an eye/instrument interface for controlling light delivery from said illumination system to said eye and for capturing and transmitting light exiting the eye to said detection system.

2. The optical apparatus according to claim 1, wherein said optical separation means includes optical components in the illumination system, the detection system or both.

3. The optical apparatus according to claim 1 or 2 additionally comprising means for modifying the light source.

4. The optical apparatus according to claim 3, wherein said means for modifying the light source modifies the vergence, spectral properties, polarization, and/or intensity of said light source.

5. The optical apparatus according to claim 1 or 2, wherein said light source comprises a tungsten-halogen lamp, an incandescent lamp, an arc lamp, a light emitting diode, a laser, or any combination thereof.

6. The optical apparatus according to claim 2, wherein said optical separation means comprises an optical element in said detection system positioned at the image point of the specularly reflected light for collecting and transmitting the specularly reflected light to one of said one or more detectors in said detection system.

7. The optical apparatus according to claim 6, wherein said optical element is a focusing mirror, a lens, a blocking aperture, a flat mirror, a prism, or a combination thereof.

8. The optical apparatus according to claim 1 additionally comprising one or more optical filters.

9. The optical apparatus according to claim 1, wherein the detection system comprises more than one detector.

10. The optical apparatus according to claim 1, wherein at least one of said one or more detectors is a photodiode, a camera, a spectrometer or a bolometer.

11. The optical apparatus according to claim 1, wherein said detection system simultaneously measures the specularly reflected light and the diffusely reflected light.

12. The optical apparatus according to claim 1, wherein said detection system sequentially measures the specularly reflected light and the diffusely reflected light.

13. A method for monitoring light remitted from an eye of a subject comprising the steps of:
 (a) illuminating one or more element of said eye with a light source;
 (b) transmitting light specularly reflected from said eye to a detection system via an optical separation means; and
 (c) separately transmitting diffusely reflected light remitted from said eye to said detection system.

14. The method according to claim 13, wherein said detection system comprises one or more detectors.

15. The method according to claim 14, wherein at least one of said one or more detectors is a photodiode, a camera, a spectrometer or a bolometer.

16. The method according to claim 13, wherein said detection system simultaneously measures the specularly reflected light and the diffusely reflected light.

17. The method according to claim 13, wherein said detection system sequentially measures the specularly reflected light and the diffusely reflected light.

18. The method according to claim 13, additionally comprising the step of transmitting said diffusely reflected light to a camera.

19. The method according to claim 13, wherein said diffusely reflected light is transmitted to said camera to obtain an image of the illumination spot on the retina of said eye and wherein said method additionally comprises the step of adjusting said illumination spot.

20. The method according to claim 13 for monitoring the health of said subject.

21. The method according to claim 13 for monitoring the health of the retina of said subject.

* * * * *

UNITED STATES PATENT AND TRADEMARK OFFICE
CERTIFICATE OF CORRECTION

PATENT NO.          : 7,896,498 B2                           Page 1 of 2
APPLICATION NO.     : 12/414437
DATED               : March 1, 2011
INVENTOR(S)         : Rejean Munger and Neil Lagali It is certified that error appears in the above-identified patent and that said Letters Patent is hereby corrected as shown below:

Column 7, line 26: Delete "L1-12" and replace with -- L1 -L2 --

In the Figures:

Figure 2A: Insert shading for Elements #42 and #44

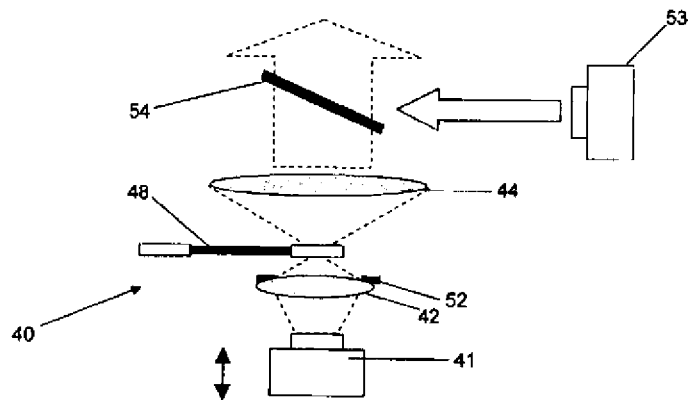

Figure 2A

Signed and Sealed this

Eighth Day of November, 2011

David J. Kappos
*Director of the United States Patent and Trademark Office*

Figure 2B: Insert shading for the ring on the figure

Figure 3: Insert two elliptical circles at number 58 of the figure